(12) United States Patent
Plata et al.

(10) Patent No.: US 9,254,253 B2
(45) Date of Patent: Feb. 9, 2016

(54) PROCESSES FOR PREPARING TOOTHPASTE COMPOSITIONS

(71) Applicant: Colgate-Palmolive Company, New York, NY (US)

(72) Inventors: Rolando Plata, Guangzhou (CN); Xiaojing Lu, Guangzhou (CN); Yuyan Zeng, Guangzhou (CN); Chengkang Tan, Guangzhou (CN)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/429,924

(22) PCT Filed: Oct. 19, 2012

(86) PCT No.: PCT/CN2012/083250
§ 371 (c)(1),
(2) Date: Mar. 20, 2015

(87) PCT Pub. No.: WO2014/059679
PCT Pub. Date: Apr. 24, 2014

(65) Prior Publication Data
US 2015/0265518 A1  Sep. 24, 2015

(51) Int. Cl.
*A61K 8/73* (2006.01)
*A61K 8/60* (2006.01)
*A61K 8/69* (2006.01)
*A61Q 11/00* (2006.01)
*A61K 8/34* (2006.01)
*A61K 8/04* (2006.01)

(52) U.S. Cl.
CPC .................. *A61K 8/737* (2013.01); *A61K 8/042* (2013.01); *A61K 8/345* (2013.01); *A61K 8/60* (2013.01); *A61K 8/69* (2013.01); *A61K 8/731* (2013.01); *A61Q 11/00* (2013.01)

(58) Field of Classification Search
USPC ....................................... 424/49, 52, 57, 602
See application file for complete search history.

(56) References Cited

U.S. PATENT DOCUMENTS

| | | |
|---|---|---|
| 5,030,444 A | 7/1991 | Hoyles et al. |
| 6,045,780 A | 4/2000 | Bixler et al. |
| 2003/0091514 A1 | 5/2003 | Stier |
| 2004/0001815 A1 | 1/2004 | Cheung |

FOREIGN PATENT DOCUMENTS

| | | |
|---|---|---|
| CN | 101396329 | 4/2009 |
| EP | 0227287 | 1/1992 |
| EP | 0368130 | 5/1994 |
| WO | WO 2005/084624 | 9/2005 |
| WO | WO 2007/061328 | 5/2007 |

OTHER PUBLICATIONS

International Search Report and Written Opinion in International Application No. PCT/CN2012/083250, mailed Jul. 25, 2013.

*Primary Examiner* — Walter Webb

(57) ABSTRACT

Disclosed herein are methods of manufacturing toothpaste compositions comprising calcium carbonate.

30 Claims, 1 Drawing Sheet

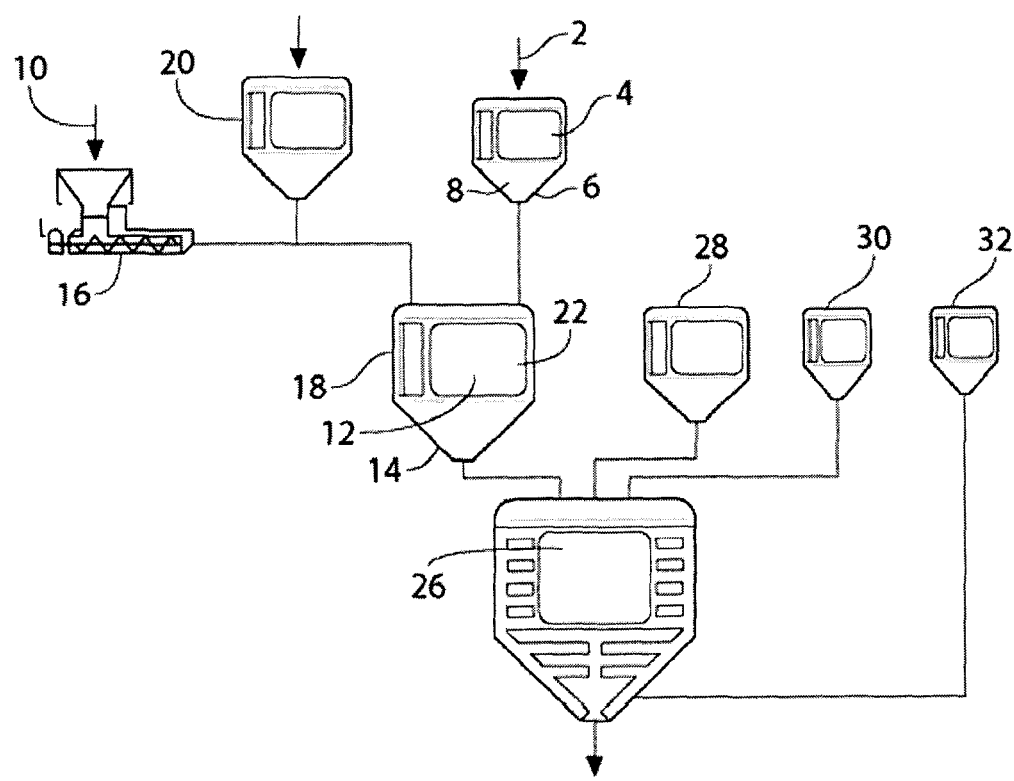

PROCESSES FOR PREPARING TOOTHPASTE COMPOSITIONS

BACKGROUND

There are problems associated with filling the toothpaste package effectively and reliably if the toothpaste exhibits the stringy effect and tailing, particularly for toothpaste formulations containing a significant proportion of calcium carbonate particles.

Specifically, traditional manufacturing processes result in toothpastes having a granular texture which is not satisfactory because consumers require toothpaste compositions which are smooth in texture.

There is accordingly a need in the art for a method of manufacturing a toothpaste composition which contains calcium carbonate particles and exhibits good rheological properties, in particular reduced stringiness and reduced tailing, and has a smooth texture.

In addition, it is well known to manufacture striped toothpastes, in which a first toothpaste phase is provided with stripes of a second phase, of toothpaste or gel, when the toothpaste is extruded as a strip from a tube or other packaging. The first toothpaste phase is typically white and the second phase is typically colored. It is an important aesthetic requirement for the consumer that the differently colored phases have a sharp boundary between them and that the different colorants do not appear to bleed from one phase into the adjacent phase.

The binder component in the toothpaste has a significant impact on the stripe quality of the extruded strip to form a stable extrudable paste including the abrasive particles and the liquid phase. In striped toothpaste formulations containing a significant proportion of calcium carbonate particles, it is known to use a binder system which controls the stripe quality. In particular, it is known to use a binder system incorporating the combination of carboxymethyl cellulose (CMC) and magnesium aluminium silicate (MAS) to provide a high stripe quality. However, the use of magnesium aluminium silicate (MAS) suffers from the problem that currently there are only a few qualified suppliers of toothpaste-grade magnesium aluminium silicate (MAS), which increases the cost and complexity of the supply chain.

There is accordingly a need in the art for a method of manufacturing a striped toothpaste composition which exhibits high stripe quality but avoids the supply chain problems of the known binder system incorporating the combination of carboxymethyl cellulose (CMC) and magnesium aluminium silicate (MAS).

SUMMARY

One aim of this invention is to provide a method of manufacturing a toothpaste composition which contains calcium carbonate particles and exhibits good rheological properties, in particular reduced stringiness and reduced tailing, and has a smooth texture.

Another aim of this invention is to a method of manufacturing a striped toothpaste composition which exhibits high stripe quality but avoids the supply chain problems of the known binder system incorporating the combination of carboxymethyl cellulose (CMC) and magnesium aluminium silicate (MAS).

According to one aspect of this invention, there is provided a method of manufacturing a toothpaste composition, the method comprising the steps of: (a) dispersing guar gum into a first aqueous medium comprising sorbitol to produce a first gellant dispersion including hydrated guar gum in a sorbitol solution; (b) dispersing at least one cellulose polymer into a second aqueous medium to produce a second gellant dispersion including hydrated cellulose polymer in an aqueous solution; (c) combining the first and second gellant dispersions to form a third gellant dispersion; and (d) mixing the third gellant dispersion with a plurality of toothpaste components, the toothpaste components including an abrasive comprising calcium carbonate particles, to form a toothpaste composition.

Optionally, in step (a) the first aqueous medium comprises of sorbitol, optionally an aqueous solution of sorbitol. Optionally, in step (a) the first gellant dispersion comprises from 0.2 to 4.0 wt % guar gum and from 96.0 to 99.8 wt % sorbitol, each being based on the weight of the first gellant dispersion. Optionally, in step (a) the first aqueous medium is at a temperature of from 20 to 40° C.

Optionally, after step (a) the guar gum is substantially fully hydrated or substantially fully dissolved in the sorbitol solution.

Optionally, in step (b) the second gellant dispersion comprises from 1.4 to 11.0 wt % of the at least one cellulose polymer and from 89.0 to 98.6 wt % water, each being based on the weight of the second gellant dispersion.

Optionally, the at least one cellulose polymer is selected from one or more of hydroxypropylmethyl cellulose (HPMC), hydroxyethylpropyl cellulose (HEPC), hydroxybutylmethyl cellulose (HBMC), and carboxymethyl cellulose (CMC). Typically, the at least one cellulose polymer comprises carboxymethyl cellulose (CMC).

Optionally, in step (b) the second aqueous medium further comprises at least one toothpaste ingredient selected from a source of fluoride ions, optionally sodium monofluorophosphate, a sweetener, optionally sodium saccharin, a bicarbonate salt, optionally sodium bicarbonate, and a carbonate salt, optionally sodium carbonate.

Optionally, in step (b) the second aqueous medium is at a temperature of from 60 to 90° C. Typically, after step (b) the at least one cellulose polymer is substantially fully hydrated or substantially fully dissolved in the aqueous solution.

Optionally, in step (d) the toothpaste components further include at least one surfactant. Typically, the at least one surfactant comprises sodium lauryl sulfate.

Optionally, the guar gum is present in an amount of from 0.05 to 0.4 wt % based on the weight of the toothpaste composition, further optionally from 0.1 to 0.2 wt % based on the weight of the toothpaste composition. Typically, the guar gum is present in an amount of from 0.13 to 0.17 wt % based on the weight of the toothpaste composition.

The guar gum dispersed in step (a) may typically be raw guar gum or a chemically unmodified guar gum.

Optionally, the calcium carbonate particles are present in an amount of from 20 to 60 wt % based on the weight of the toothpaste composition, further optionally from 35 to 50 wt % based on the weight of the toothpaste composition. Typically, the calcium carbonate particles are present in an amount of from 40 to 45 wt % based on the weight of the toothpaste composition.

Optionally, the at least one cellulose polymer is present in an amount of from 0.5 to 2.5 wt % based on the weight of the toothpaste composition, further optionally from 0.75 to 1.5 wt % based on the weight of the toothpaste composition.

In one preferred composition, the guar gum is present in an amount of about 0.15 wt % based on the weight of the toothpaste composition and carboxymethyl cellulose (CMC) is present in an amount of about 1 wt % based on the weight of the toothpaste composition.

Optionally, the sorbitol is present in an amount of from 10 to 25 wt % based on the weight of the toothpaste composition, further optionally from 12 to 18 wt % based on the weight of the toothpaste composition.

In some preferred embodiments, the toothpaste composition is a first phase of a two-phase toothpaste and further comprising packaging the toothpaste composition in a package for forming a striped strip when the toothpaste is extruded as a strip from the package. Typically, the toothpaste composition comprises a first white phase of the two-phase toothpaste, the two-phase toothpaste further comprising a second colored phase. Typically, the second colored phase comprises a toothpaste composition manufactured according to the method of the invention and a colorant.

The present invention also provides a packaged two-phase toothpaste manufactured according to the method of the invention.

The compositions may contain additional therapeutic and non-therapeutic components.

This invention is predicated on the finding by the present inventors that in toothpaste comprising calcium carbonate particles as an abrasive, and a binder system which comprises guar gum and at least one cellulose polymer, by modifying the manufacturing method a smooth paste can reliably be manufactured. Furthermore, the resultant smooth toothpaste avoid or reduce the stringy and tailing problems of known toothpastes and, when used in particular in striped toothpaste comprising calcium carbonate particles as an abrasive, can provide a high stripe quality.

BRIEF DESCRIPTION OF THE DRAWING

FIG. 1 is a schematic diagram of a manufacturing plant for manufacturing toothpaste according to an embodiment of the present invention.

DETAILED DESCRIPTION

It should be understood that the detailed description and specific examples, while indicating embodiments of the invention, are intended for purposes of illustration only and are not intended to limit the scope of the invention.

As referred to herein, all compositional percentages are by weight of the total composition, unless otherwise specified.

The invention described herein includes a method of manufacturing a toothpaste composition, which comprises guar gum and at least one cellulose polymer as a gellant binder system, sorbitol as a humectant and an abrasive comprising calcium carbonate particles.

As used herein, the phrase "substantially free" means that the particular component comprises less than 10% of a particular component. For example, a binder system is "substantially free" of magnesium aluminum silicate refers to a binder system that comprises less than 10% of magnesium aluminium silicate.

Some embodiments of the present invention provide compositions wherein the binder system is substantially free of the magnesium aluminium silicate. In some embodiments, the binder system comprises less than 7.5% magnesium aluminium silicate. In some embodiments, the binder system comprises less than 5% magnesium aluminium silicate. In some embodiments, the binder system comprises less than 4% magnesium aluminium silicate. In some embodiments, the binder system comprises less than 3% magnesium aluminium silicate. In some embodiments, the binder system comprises less than 2% magnesium aluminium silicate. In some embodiments, the binder system comprises less than 1% magnesium aluminium silicate. In some embodiments, the binder system comprises less than 0.5% magnesium aluminium silicate.

A manufacturing method for a toothpaste composition according to an embodiment of the invention is illustrated in FIG. 1.

Referring to FIG. 1, in a first step, guar gum 2 is dispersed into a first aqueous medium 4 which is in a first tank 6, optionally including a mixer (not shown). The first aqueous medium 4 comprises sorbitol, optionally an aqueous solution of sorbitol. The first aqueous medium is typically at a temperature of from 20 to 40° C.

This dispersion step produces a first gellant dispersion 8 including hydrated guar gum in a sorbitol solution. In the first gellant dispersion, the guar gum is substantially fully hydrated, and substantially fully dissolved in the sorbitol solution to form a first gel phase. Typically, the first gellant dispersion comprises from 0.2 to 4.0 wt % guar gum and from 96.0 to 99.8 wt % sorbitol, each being based on the weight of the first gellant dispersion.

In a second step, which may be before, after or simultaneous with the first step, at least one cellulose polymer 10, as described above, is dispersed into a second aqueous medium 12 to produce a second gellant dispersion 14 including hydrated cellulose polymer in an aqueous solution. The second gellant dispersion 14 forms a second gel phase, in which the at least one cellulose polymer is fully hydrated and fully dissolved. The second aqueous medium is typically at a temperature of from 60 to 90° C.

Typically, the second gellant dispersion 14 comprises from 1.4 to 11.0 wt % of the at least one cellulose polymer and from 89.0 to 98.6 wt % water, each being based on the weight of the second gellant dispersion. The second aqueous medium 12 may further comprise at least one toothpaste ingredient selected from a source of fluoride ions, optionally sodium monofluorophosphate, a sweetener, optionally sodium saccharin, and additionally any acid or base required to adjust the pH of the composition, such as a bicarbonate salt, optionally sodium bicarbonate, and a carbonate salt, optionally sodium carbonate.

In the illustrated embodiment, the at least one cellulose polymer, such as carboxymethyl cellulose, is provided as a powder and pumped by an eductor 16 into a gel tank 18. Water, optionally including the at least one toothpaste ingredient dissolved or dispersed therein, is stored in a supply tank 20 and supplied therefrom into the gel tank 18. The gel tank 18 optionally includes a mixer (not shown). Thus in this embodiment the second gellant dispersion 14 is formed in the gel tank 18.

Thereafter, the first and second gellant dispersions 8, 14 are combined to form a third gellant dispersion 22. In the illustrated embodiment, the first gellant dispersion 8 is supplied from the first tank 6 into the gel tank 18 which already contains the second gellant dispersion 8 and the first and second gellant dispersions 8, 14 are mixed together to form a homogeneous mixed gel phase.

Thereafter the third gellant dispersion 22 is typically mixed with a plurality of toothpaste components. The toothpaste components may include an abrasive comprising calcium carbonate to form a toothpaste composition. In some embodiments, the calcium carbonate is present as particles. In the illustrated embodiment, the third gellant dispersion 22 is supplied from the gel tank 18 into a mixer 26, and additional component tanks 28, 30, 32 supply additional components such as, respectively, abrasive, flavour and surfactant. Any water insoluble agents, such as triclosan, may be solubilized in the flavor oils to be included in the toothpaste. Additional components such as pigments, such as $TiO_2$, may be added at this stage to mixer 26. The resultant mixture is agitated until a homogeneous toothpaste composition is formed.

In the mixer 26, which may be a high speed/vacuum mixer, the mixture is typically mixed at high speed for a period in the range from 5 to 30 minutes, typically under a vacuum of 20 to 50 mm of Hg. The resultant product is a homogeneous, semi-solid, extrudable paste.

The guar gum and the at least one cellulose polymer used in the method of the invention as described above comprise a binder system for the toothpaste composition.

In the binder system, optionally the guar gum is present in an amount of from 0.05 to 0.4 wt % based on the weight of the composition, further optionally from 0.1 to 0.2 wt % based on the weight of the composition. Typically, the guar gum is present in an amount of from 0.13 to 0.17 wt % based on the weight of the composition. Most typically, the guar gum is present in an amount of about 0.15 wt % based on the weight of the composition.

In some embodiments, the guar gum is raw guar gum or is chemically unmodified guar gum.

Typically, the at least one cellulose polymer is present as a salt, for example the sodium salt.

In the binder system, optionally the at least one cellulose polymer is selected from one or more of hydroxypropylmethyl cellulose (HPMC), hydroxyethylpropyl cellulose (HEPC), hydroxybutylmethyl cellulose (HBMC), and carboxymethyl cellulose (CMC). Typically, the at least one cellulose polymer comprises carboxymethyl cellulose (CMC), for example in the form of sodium carboxymethyl cellulose. In one embodiment the at least one cellulose polymer comprises a mixture of cellulose materials having different molecular weight.

Optionally, the at least one cellulose polymer is present in an amount of from 0.5 to 2.5 wt % based on the weight of the composition, further optionally, from 0.75 to 1.5 wt % based on the weight of the composition.

In one preferred embodiment, the guar gum is present in an amount of about 0.15 wt % based on the weight of the composition and carboxymethyl cellulose (CMC) is present in an amount of about 1 wt % based on the weight of the composition.

Optionally, the binder system does not comprise any magnesium aluminum silicate.

In addition to the cellulose and guar gum binders, the toothpaste compositions made according to the method of the invention may also include a polymeric adherent material that attaches to the surface of a mammalian tooth and/or to the heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth.

For example, the toothpaste composition may additionally include poly (ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises (PVM/MA). In an embodiment, a copolymer comprises poly (methylvinylether/maleic anhydride). In another embodiment, a copolymer comprises poly (methylvinylether/maleic acid). In another embodiment, a copolymer comprises poly (methylvinylether/maleic acid) half esters. In another embodiment, a copolymer comprises poly (methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average).

Commercially-available polymers may be used in the toothpaste compositions made according to the invention. It is understood that over time, the exact size, weight and/or composition of a commercially-available polymer may change. Based on the disclosure set forth herein, the skilled artisan will understand how to determine whether such polymers are useful in the toothpaste compositions made according to the invention.

In addition to the guar gum and at least one cellulose polymer, the toothpaste composition may additionally include, other gum bases or thickening agents, such as carrageenan (Iris moss), xanthan gum, starch, polyvinyl pyrrolidone and amorphous silicas, or any combination thereof.

In the abrasive system of the toothpaste composition, optionally the calcium carbonate particles are present in an amount of from 20 to 60 wt % based on the weight of the composition, further optionally from 35 to 50 wt % based on the weight of the composition. Typically, the calcium carbonate particles are present in an amount of from 40 to 45 wt % based on the weight of the composition. Most typically, the calcium carbonate particles are present in an amount of about 42 wt % based on the weight of the composition. The calcium carbonate may comprise precipitated calcium carbonate.

The toothpaste compositions may further comprise, in addition to the calcium carbonate particles, one or more abrasive particulates. Any abrasive particulates may be used and may be selected from sodium bicarbonate, calcium phosphate (e.g., dicalcium phosphate dihydrate), calcium pyrophosphate calcium sulfate, silica, iron oxide, aluminium oxide, perlite, plastic particles, e.g., polyethylene, and combinations thereof. Any type of silica may be used, such as hydrated silica, precipitated silica or silica gel. Optionally, the toothpaste composition further comprises, as a thickener and also as an abrasive, silica particles in an amount of from 1 to 3 wt % based on the weight of the composition.

In an embodiment, the toothpaste composition comprises silica that has a particle size and an amount and distribution in the toothpaste composition so that the silica has a dual function, and functions not only as a dentin tubule-occluding particulate but also as an abrasive particulate. Such a dual function particulate may be provided by a commercially available silica such as INEOS AC43, available in commerce from Ineos Silicas, Warrington, United Kingdom. In an embodiment, such silica has a median particle size less than 8 μm, for example from 3 μm to 5 μm.

The compositions of the present invention may further comprise an abrasive useful for example as a polishing agent. Any orally acceptable abrasive can be used, but type, fineness, (particle size) and amount of abrasive should be selected so that tooth enamel is not excessively abraded in normal use of the composition. Suitable abrasives include silica, for example in the form of precipitated silica or as admixed with alumina, insoluble phosphates, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In an embodiment, the abrasive particles may be initially present in the toothpaste composition having the desired particle size, or may be initially present in the composition at a larger size, so long as the structure of the particles is such that it fractures or breaks into the desired particle size upon application of mechanical force by, e.g., a toothbrush, when brushing.

The dentifrice composition according to the invention comprises an orally acceptable vehicle, which includes sorbitol. As used herein, an "orally acceptable vehicle" refers to a material or combination of materials that are safe for use in the compositions of the invention, commensurate with a reasonable benefit/risk ratio. Optionally, the orally acceptable vehicle comprises sorbitol which is present in an amount of from 10 to 25 wt % based on the weight of the composition, further optionally from 12 to 18 wt % based on the weight of the composition.

The composition may additionally contain any conventional excipients or carriers, although these will vary depending on the dosage form or means of dosage selected. Excipients or carriers in addition to sorbitol can include, for example, humectants, glycerin, xylitol, and/or propylene glycol, water or other solvents.

Surfactants may be included, if desired. Examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoyl sarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly (ethylene oxide) with fatty acids, fatty, alcohols, fatty amides and other fatty moieties, and with propylene oxide and polypropylene oxides.

In an embodiment, the oral composition includes a surfactant system that is sodium lauryl sulfate (SLS).

According to a preferred aspect of this invention, the toothpaste made according to the method of the invention may be used in a two-phase toothpaste packaged in a package for forming a striped strip when the toothpaste is extruded as a strip from the package. At least one of the two phases of the two-phase toothpaste comprises the toothpaste composition manufactured according to the method of the invention, which comprises an orally acceptable vehicle including sorbitol, an abrasive comprising calcium carbonate particles and a binder system comprising guar gum and at least one cellulose polymer.

Optionally, the two-phase toothpaste comprises a first white phase of the two-phase toothpaste, the first white phase having the toothpaste composition manufactured according to the invention and a second colored phase. The second colored phase may comprise a toothpaste composition manufactured according to the invention and a colorant. Alternatively, the second colored phase may comprise an alternative toothpaste composition or a gel.

The use, in a striped toothpaste including a white toothpaste phase comprising calcium carbonate particles as an abrasive and a colored phase, of a binder system in the white toothpaste phase which comprises guar gum and at least one cellulose polymer can minimize mixing of the white toothpaste phase and the colored phase after the striped toothpaste has been extruded as a strip from a package.

The toothpaste composition may include any other therapeutic, cosmetic, and/or aesthetic materials as may be desired. Examples include desensitizing agents (e.g. a nitrate salt, an arginine ester, a bicarbonate salt, potassium nitrate, an arginine-bicarbonate-phytate complex, potassium citrate, and arginine, among others), a chemical whitening agent (such as a peroxide releasing compound), an opaque whitening agent (such as hydroxyapatite) and an anticalculus agent.

The toothpaste composition may also comprise one or more further agents typically selected from an anti-plaque agent, a whitening agent, desensitizing agent, antimicrobial agent, antibacterial agent, cleaning agent, a flavouring agent, a sweetening agent, adhesion agents, surfactants, foam modulators, abrasives, pH modifying agents, humectants, mouth feel agents, colorants, abrasive, tartar control (anticalculus) agent, fluoride ion source, saliva stimulating agent, nutrient and combinations thereof. The compositions of the invention optionally comprise a fluoride ion source and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N, N'-tris(2-ethanol)-dihydrofluoride), and mixtures thereof. One or more fluoride ion sources are optionally present in an amount providing a clinically efficacious amount of soluble fluoride ion to the oral composition. Optionally, the toothpaste composition further comprises sodium monofluorophosphate in an amount of from 0.75 to 1.5 wt % based on the weight of the composition.

Colorants may be used in a single phase toothpaste or a two-phase toothpaste for forming a striped toothpaste. Such colorants may be selected from pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, magnesium silicate, silica, titanium dioxide, zinc oxide, red, yellow, brown and black iron oxides, ferric ammonium ferrocyanide, manganese violet, ultramarine, titanated mica, bismuth oxychloride, and mixtures thereof. One or more colorants are optionally present in a total amount of about 0.001% to about 20%, for example about 0.01% to about 10% or about 0.1% to about 5%.

Optionally, the toothpaste composition further comprises titanium dioxide in an amount of from 0.05 to 0.15 wt % based on the weight of the composition. Such titanium dioxide addition has been found to whiten the slightly yellowish appearance of the toothpaste caused by the addition of the guar gum binder.

The toothpaste composition manufactured according to the method of the invention may be administered to or applied to a human or other animal subject. The composition is suitable for administration or application to the oral cavity of a human or animal subject.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

A toothpaste composition having the formula indicated in Table 1 was prepared using the method of the invention as described above. In particular, the guar gum was separately dispersed in a sorbitol solution in a dedicated tank so as to be fully hydrated. Carboxymethyl cellulose, and the minor ingredients sodium monofluorophosphate, sodium bicarbonate, sodium carbonate and sodium saccharin, were dispersed in hot water in a gel tank and the carboxymethyl cellulose was fully hydrated. After complete dissolution of the carboxymethyl cellulose, the mixture of guar gum and sorbitol was added to the gel tank. The mixture was mixed, and the other ingredients were added to the gel tank. All amounts are in wt %.

TABLE 1

| Ingredient | Ex. 1 |
| --- | --- |
| Sorbitol (70 wt % aqueous solution) | 21 |
| Guar gum | 0.15 |
| Sodium saccharin | 0.27 |
| Sodium monofluorophosphate | 1.1 |
| CMC | 1 |
| Sodium bicarbonate | 0.1 |
| Sodium carbonate | 0.4 |
| Silica | 2 |
| Calcium carbonate | 42 |
| Titanium dioxide | 0.1 |
| Sodium lauryl sulfate | 2 |
| Methyl paraben | 0.1 |
| Propyl paraben | 0.02 |
| Water | 28.76 |
| Flavor | 1 |
| Total | 100 |

| Ingredient | Colored phase |
| --- | --- |
| Sorbitol (70 wt % aqueous solution) | 21 |
| Guar gum | 0.15 |
| Sodium saccharin | 0.27 |
| Sodium monofluorophosphate | 1.1 |
| CMC | 1 |
| Sodium bicarbonate | 0.1 |
| Sodium carbonate | 0.4 |
| Silica | 2 |
| Calcium carbonate | 42 |
| Titanium dioxide | 0.1 |
| Sodium lauryl sulfate | 2 |

TABLE 1-continued

| Methyl paraben | 0.1 |
| --- | --- |
| Propyl paraben | 0.02 |
| Water | 28.7533 |
| Flavor | 1 |
| CI Pigment Green 7 | 0.0067 |
| Total | 100 |

The toothpaste composition produced according to the method of Example 1 exhibited a smooth non-granular texture.

The viscosity of the composition of Example 1 was evaluated over an aging test of a period of 1 week. The initial viscosity and final viscosity, after a period of 1 week, of the composition of Example 1 were acceptable for use as a commercial toothpaste.

Furthermore, the rheological properties of composition of Example 1 were found to provide a toothpaste composition which stays on the mixer blade as a common non-flowing mass.

In contrast, some toothpaste compositions incorporating calcium carbonate and other binder systems than guar gum/CMC exhibit a "tailing" phenomenon in which the toothpaste composition flows under gravity to form trails extending downwardly from the blade. The resultant toothpaste can be difficult to use in a package filling process. Accordingly, it may be seen that the addition of guar gum to the CMC binder composition made according to method of the invention also solves the problem of trailing of the composition. The compositions produced according to the invention, as represented by Example 1, solve the trailing issue in toothpaste compositions including calcium carbonate and CMC.

Other rheological properties of the composition of Example 1 were tested, in particular the flow property, thixotropy, yield stress and creep recovery, and these results showed that the binder system of CMC and guar gum provided three dimensional structure to the toothpaste compositions produced according to the invention.

In summary therefore, the inventors have found by their experimental investigations and results that that the binder system of CMC and guar gum provided in the calcium carbonate-containing toothpaste compositions produced according to the invention a smooth composition which had the desired viscosity and rheology and also solved the problem of stringiness and tailing in known toothpaste formulations.

The composition of Example 1 was also evaluated to determine the ability of the composition to provide a high quality stripe when used in a striped toothpaste.

The composition shown in Table 1 was employed to make a striped toothpaste, forming a first white phase. The second colored phase comprised of the composition shown in Table 1A.

The stripe quality was tested by extruding the striped toothpaste and quantitatively evaluating the stripe quality according to a stripe quality index (SQI) numerical scale where 1 represents the worst stripe quality and 5 represents the best stripe quality. Ten data points were employed for the testing of each toothpaste, each data point corresponding to a respective property of a respective extrusion (A=stripe definition, B=stripe consistency of the first short ribbons during extrusion, C=stripe definition, D=stripe consistency of the first long ribbons during extrusion, E=stripe definition, F=stripe consistency of the second short ribbons during extrusion; G=stripe definition, H=stripe consistency of the second long ribbons during extrusion; I=stripe definition, J=stripe consistency of the last short ribbons during extrusion).

The results are shown in Table 2:

TABLE 2

| Stripe Quality Index | Example 1 |
|---|---|
| A | 3.0 |
| B | 2.5 |
| C | 5.0 |
| D | 5.0 |
| E | 5.0 |
| F | 5.0 |
| G | 5.0 |
| H | 5.0 |
| I | 0.4 |
| J | 2.0 |
| Average SQI value | 4.1 |

The composition of Example 1 incorporating the combination of guar gum and CMC as a binder provided good stripe quality, with a clean separation between the white phase and the colored stripes.

This composition produced according to the invention therefore can produce a high quality striped toothpaste.

In summary therefore, the inventors have found by their experimental investigations and results that that the method of the invention to produce a toothpaste including a binder system of CMC and guar gum provided in the calcium carbonate-containing toothpaste composition not only the desired viscosity and rheology and solved the problem of stringiness and tailing in known toothpaste formulations, but also provided high stripe quality in striped toothpastes.

Comparative Example 1

A toothpaste composition having the formula indicated in Table 1 was prepared using a method not according to the invention.

In particular, the binder system of guar gum and carboxymethyl cellulose was mixed together with the minor ingredients of sodium monofluorophosphate, sodium bicarbonate, sodium carbonate and sodium saccharin. This mixture was then dispersed into a solution of sorbitol in hot water in a gel tank. The mixture was mixed thoroughly with the aim of achieving full hydration of the guar gum and the carboxymethyl cellulose. The remaining ingredients were added to the gel tank and the mixture fully mixed to form a toothpaste composition.

However, the toothpaste composition produced according to the method of Comparative Example 1 exhibited a granular texture, with an appearance that is not acceptable to the consumer.

The invention claimed is:

1. A method of manufacturing a toothpaste composition, the method comprising the steps of:
  (a) dispersing guar gum into a first aqueous medium comprising sorbitol to produce a first gellant dispersion including hydrated guar gum in a sorbitol solution;
  (b) dispersing at least one cellulose polymer into a second aqueous medium to produce a second gellant dispersion including hydrated cellulose polymer in an aqueous solution;
  (c) combining the first and second gellant dispersions to form a third gellant dispersion; and
  (d) mixing the third gellant dispersion with a plurality of toothpaste components, the toothpaste components including an abrasive comprising calcium carbonate particles, to form a toothpaste composition.

2. The method according to claim 1 wherein in step (a), the first aqueous medium comprises of sorbitol, optionally an aqueous solution of sorbitol.

3. The method according to claim 1 wherein in step (a) the first gellant dispersion comprises from 0.2 to 4.0 wt % guar gum and from 96.0 to 99.8 wt % sorbitol, each being based on the weight of the first gellant dispersion.

4. The method according to claim 1 wherein in step (a) the first aqueous medium is at a temperature of from 20 to 40° C.

5. The method according to claim 1 wherein after step (a) the guar gum is substantially fully hydrated.

6. The method according to claim 1 wherein after step (a) the guar gum is substantially fully dissolved in the sorbitol solution.

7. The method according to claim 1 wherein in step (b) the second gellant dispersion comprises from 1.4 to 11.0 wt % of the at least one cellulose polymer and from 89.0 to 98.6 wt % water, each being based on the weight of the second gellant dispersion.

8. The method according to claim 1 wherein the at least one cellulose polymer is selected from one or more of hydroxypropylmethyl cellulose (HPMC), hydroxyethylpropyl cellulose (FIEPC), hydroxybutylrneihyl cellulose (HBMC), and carboxymethyl cellulose (CMC).

9. The method according to claim 8 wherein the at least one cellulose polymer comprises carboxymethyl cellulose (CMC).

10. The method according to claim 1 wherein in step (b) the second aqueous medium further comprises at least one toothpaste ingredient selected from a source of fluoride ions, optionally sodium monofluorophosphate, a sweetener, optionally sodium saccharin, a bicarbonate salt, optionally sodium bicarbonate, and a carbonate salt, optionally sodium carbonate.

11. The method according to claim 1 wherein in step (b) the second aqueous medium is at a temperature of from 60 to 90° C.

12. The method according to claim 1 wherein after step (b) the at least one cellulose polymer is substantially fully hydrated.

13. The method according to claim 1 wherein after step (b) at least one cellulose polymer is substantially fully dissolved in the aqueous solution.

14. The method according to claim 1, wherein in step (d) the toothpaste components further include at least one surfactant.

15. The method according to claim 14, wherein the at east one surfactant comprises sodium lauryl sulfate.

16. The method according to claim 1 wherein the guar gum is present in an amount of from 0.05 to 0.4 wt % based on the weight of the toothpaste composition.

17. The method according to claim 16 wherein the guar gum is present in an amount of from 0.1 to 0.2 wt % based on the weight of the toothpaste composition.

18. The method according to claim 17 wherein the guar gum is present in an amount of from 0.13 to 0.17 wt % based on the weight of the toothpaste composition.

19. The method according to claim 1 wherein the guar gum dispersed in step (a) is raw guar gum.

20. The method according to claim 1 wherein the guar gum dispersed in step (a) is chemically unmodified guar gum.

21. The method according to claim 1 wherein the calcium carbonate particles are present in an amount of from 20 to 60 wt % based on the weight of the toothpaste composition.

22. The method according to claim 21 wherein the calcium carbonate particles are present in an amount of from 35 to 50 wt % based on the weight of the toothpaste composition.

23. The method according to claim 22 wherein the calcium carbonate particles are present in an amount of from 40 to 45 wt % based on the weight of the toothpaste composition.

24. The method according to claim 1 wherein the at least one cellulose polymer is present in an amount of from 0.5 to 2.5 wt % based on the weight of the toothpaste composition.

25. The method according to claim 24 wherein the at least one cellulose polymer is present in an amount of from. 0.75 to 1.5 wt % based on the weight of the toothpaste composition.

26. The method according to claim 25 wherein the guar gum is present in an amount of about 0.15 wt % based on the weight of the toothpaste composition and carboxymethyl cellulose (CMC) is present in an amount of about 1 wt % based on the weight of the toothpaste composition.

27. The method according to claim 1 wherein the sorbitol is present in an amount of from 10 to 25 wt % based on the weight of the toothpaste composition.

28. The method according to claim 27 wherein the sorbitol is present in an amount of from 12 to 18 wt % based on the weight of the toothpaste composition.

29. The method according to claim 1 wherein the toothpaste composition is a first phase of a two-phase toothpaste and further comprising packaging the toothpaste composition in a package for forming a striped strip when the toothpaste is extruded as a strip from the package.

30. The method according to claim 29 wherein the toothpaste composition comprises a first white phase of the two-phase toothpaste, the two-phase toothpaste further comprising a second colored phase.

* * * * *